(12) United States Patent
Georgakoudi et al.

(10) Patent No.: US 6,697,652 B2
(45) Date of Patent: Feb. 24, 2004

(54) FLUORESCENCE, REFLECTANCE AND LIGHT SCATTERING SPECTROSCOPY FOR MEASURING TISSUE

(75) Inventors: Irene Georgakoudi, Waltham, MA (US); Vadim Backman, Cambridge, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 226 days.

(21) Appl. No.: 09/766,879

(22) Filed: Jan. 19, 2001

(65) Prior Publication Data

US 2002/0143243 A1 Oct. 3, 2002

(51) Int. Cl.[7] ................................................. A61B 5/00
(52) U.S. Cl. ..................... 600/310; 600/476; 600/477; 600/478; 600/407; 356/342
(58) Field of Search ............................ 600/310, 473, 600/476, 477, 478, 178, 180, 181, 314, 342, 407, 587, 590, 593; 436/171, 172, 63; 356/432, 369, 367, 364, 342

(56) References Cited

U.S. PATENT DOCUMENTS

| 4,768,513 A | | 9/1988 | Suzuki ........................ 128/634 |
|---|---|---|---|
| 4,773,097 A | | 9/1988 | Suzaki et al. ................... 382/6 |
| 5,201,318 A | | 4/1993 | Rava et al. .................. 128/665 |
| 5,280,788 A | | 1/1994 | Janes et al. .................. 128/665 |
| 5,304,173 A | * | 4/1994 | Kittrell et al. ................ 600/477 |
| 5,318,024 A | * | 6/1994 | Kittrell et al. ................ 600/476 |
| 5,345,941 A | * | 9/1994 | Rava et al. .................. 600/476 |
| 5,419,323 A | * | 5/1995 | Kittrell et al. ................ 600/476 |
| 5,421,337 A | * | 6/1995 | Richards-Kortum et al. ..... 600/477 |
| 5,452,723 A | * | 9/1995 | Wu et al. .................... 600/342 |
| 5,562,100 A | * | 10/1996 | Kittrell et al. ............... 600/476 |
| 5,582,168 A | | 12/1996 | Samuels et al. ............. 128/663 |
| 5,697,373 A | | 12/1997 | Richards-Kortum et al. .............. 128/664 |
| 6,008,889 A | | 12/1999 | Zeng et al. .................... 356/73 |
| 6,091,984 A | * | 7/2000 | Perelman et al. ............ 600/476 |
| 6,321,111 B1 | * | 11/2001 | Perelman et al. ............ 600/477 |
| 6,404,497 B1 | * | 6/2002 | Backman et al. ............ 356/369 |
| 2002/0093563 A1 | | 7/2002 | Cline et al. .................... 348/65 |

FOREIGN PATENT DOCUMENTS

| EP | 0 449 883 | 10/1991 |
|---|---|---|
| JP | 2002-95624 | 4/2002 |
| WO | WO 99/18845 | 4/1999 |
| WO | WO 00/42912 | 7/2000 |
| WO | WO 01/34031 | 5/2001 |

OTHER PUBLICATIONS

Richards–Kortum, R., et al., "A One–Layer Model of Laser–Induced Fluorescence for Diagnosis of Disease in Human Tissue: Applications to Atherosclerosis," IEEE Transactions on Biomedical Engineering, 36 (12) : 1222–1232.

(List continued on next page.)

Primary Examiner—Henry Bennett
Assistant Examiner—Fadi H. Dahbour
(74) Attorney, Agent, or Firm—Bowditch & Dewey, LLP

(57) ABSTRACT

Preferred embodiments of the present invention utilize a plurality of spectroscopic techniques to measure characteristics of tissue useful in the diagnosis of disease. Fluorescence, reflectance and light scattered spectra can be measured and processed to determine the size, distribution and/or composition of tissue. The methods and systems can be used particularly in the early detection of carcinoma within tissue in vivo and in vitro.

48 Claims, 13 Drawing Sheets

OTHER PUBLICATIONS

Perelman, L. T., et al., "Observation of Periodic Fine Structure in Reflectance from Biological Tissue: A New Technique for Measuring Nuclear Size Distribution," *Physical Review Letters* 80(3):627–630 (1998).

Backman, V., et al., "Detection of Preinvasive Cancer Cells," *Nature* 406:35–36 (2000).

Zonios, G., et al., "Diffuse Reflectance Spectroscopy of Human Adenomatous Colon Polyps In Vivo," *Applied Optics* 38(31): 6628–6637 (1999).

Panjehour, M., et al., "Endoscopic Fluorescence Detection of High–Grade Dysplasia In Barrett's Esophagus," *Gastroeneterology* 111:93–101 (1996).

Wallace, M.B., et al., "Endoscopic Detection of Dysplasia In Patients with Barrett's Esophagus Using Light–Scattering Spectroscopy," *Gastroenterology* 119:667–682 (2000).

Zhang, Q., et al., "Turbidity–Free Fluorescence Spectroscopy of Biological Tissue," *Optics Letters* 25(19):1451–1453 (2000).

Georgakoudi, I., et al., "Fluorescence, Reflectance and light Scattering Spectroscopy for Evaluating Dysplasia in Patients with Barrett's Esophagus," *Gastroenterology*, pp. 1–15, downloaded Dec. 6, 2000 from http://www.gastro--central.org/view.

Yang, C. et al., "Phase Dispersion Optical Tomography," *Optics Letters* pp. 1–12 (Abstract) (2000).

"Tri–Modal Spectroscopy—A New Approach to Spectroscopic Detection of Cervical Neoplasia in Vivo," (abstract).

Georgakoudi, I. et al., "Spectroscopy for Detection of Cancer," Presented at the APS Mar. 2001 Meeting in Seattle Washington.

Yang, C., et al., "Feasibility of Field–Base Light Scattering Spectroscopy," *Journal of Biomedical Optics* (5)2:138–143 (Apr. 2000).

* cited by examiner

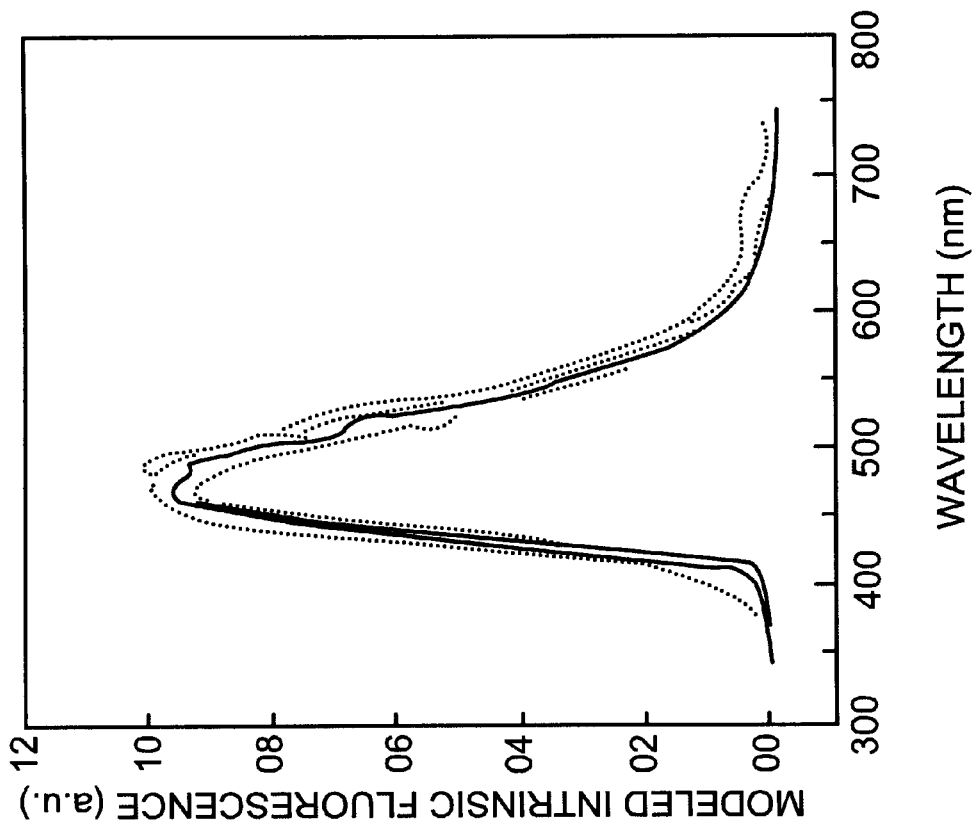
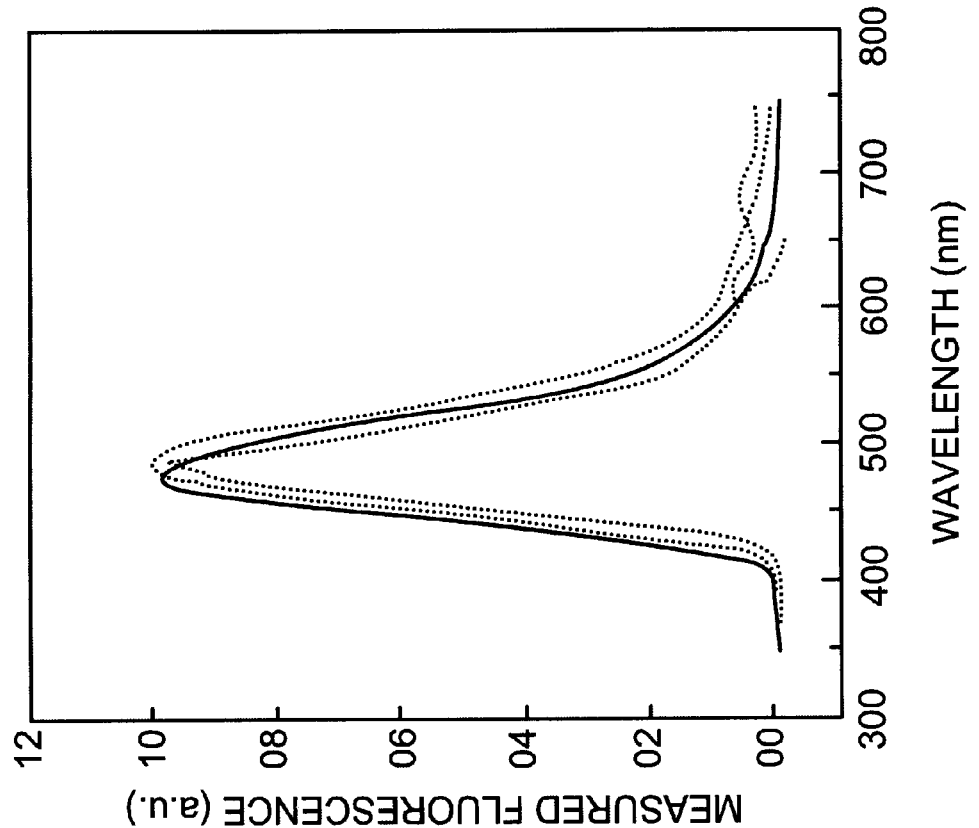
Figure 3D
Figure 3C

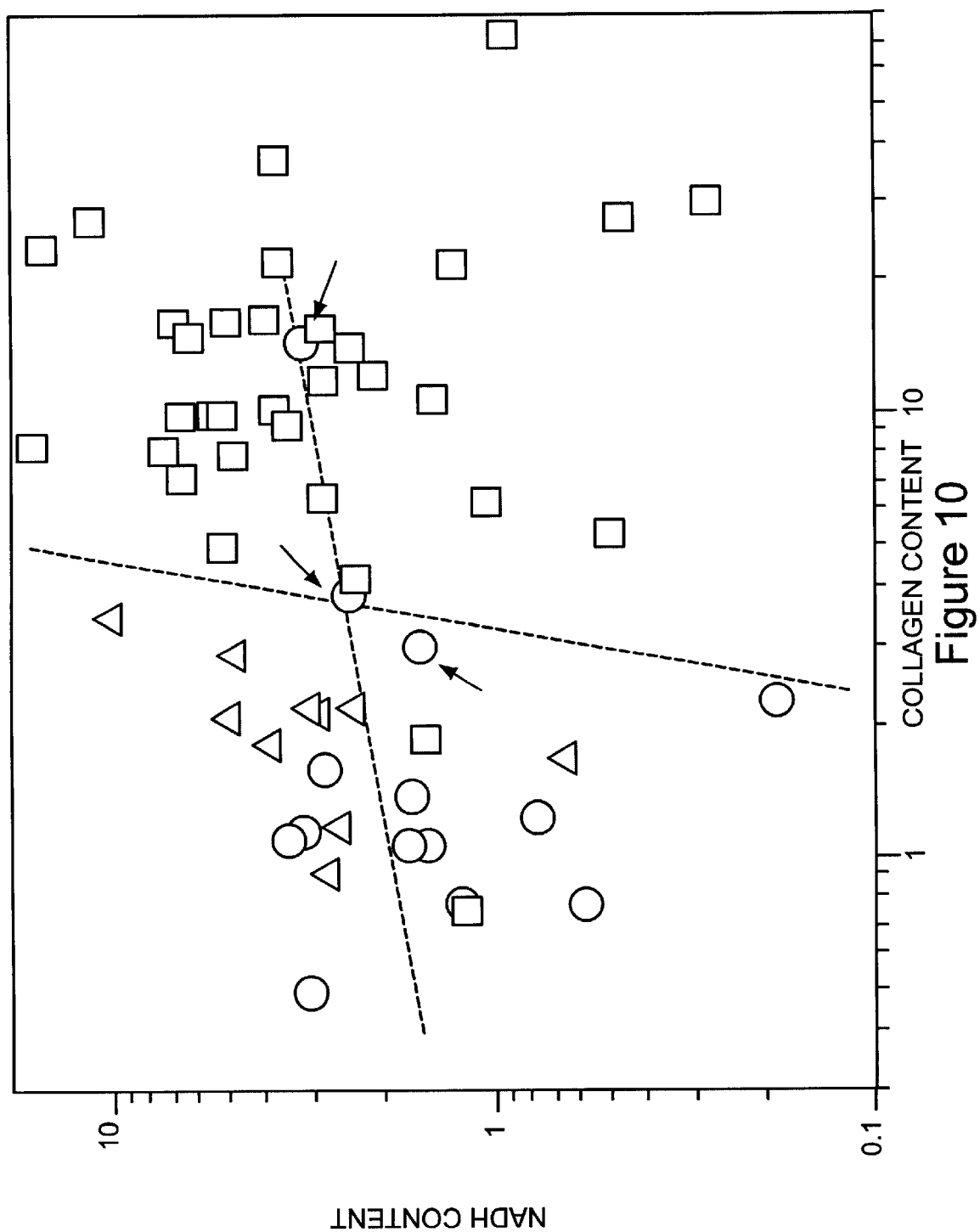

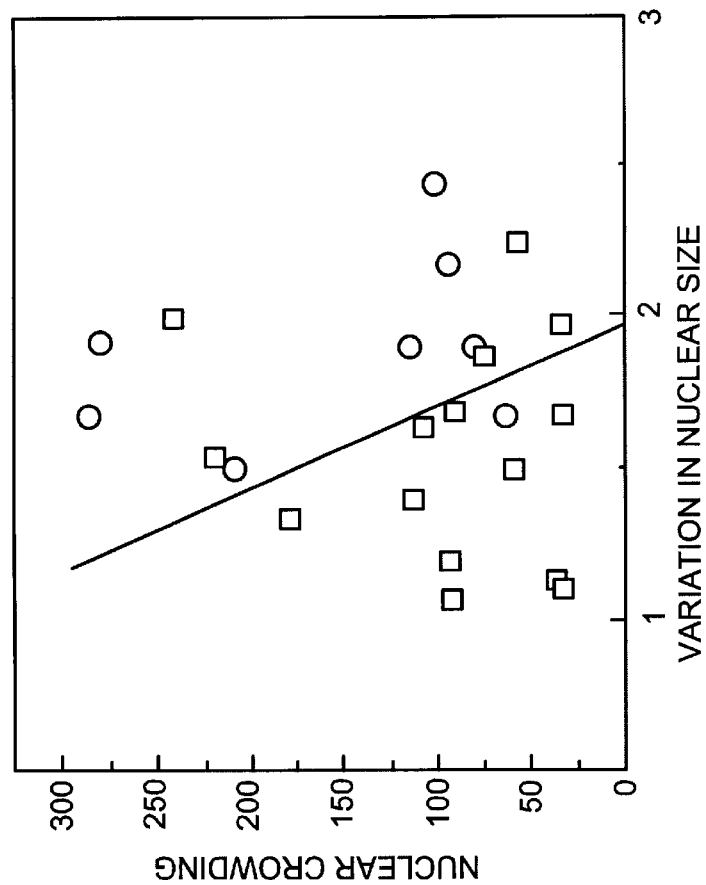

FLUORESCENCE, REFLECTANCE AND LIGHT SCATTERING SPECTROSCOPY FOR MEASURING TISSUE

GOVERNMENT SUPPORT

The invention was supported, in whole or in part, by a grants P41RR02594, 1F32CA80345 and CA53717 from the National Institutes for Health. The Government has certain rights in the invention.

BACKGROUND OF THE INVENTION

Adenocarcinoma of the lower esophagus develops almost exclusively in patients with Barrett's esophagus (BE), a condition characterized by the presence of metaplastic columnar epithelium. While the prognosis of patients diagnosed with adenocarcinoma is poor, the chances of successful treatment increase significantly if the disease is detected at the dysplastic stage. The surveillance of patients with BE for dysplasia is challenging in two respects. First, dysplasia is not visible during routine endoscopy. Thus, numerous random biopsies are required. Second, the histopathologic diagnosis of dysplasia is problematic, as there is poor inter-observer agreement on the classification of a particular specimen, even among expert gastrointestinal pathologists. Optical techniques, such as fluorescence, may significantly enhance the endoscopist's ability to detect these early dysplastic changes in BE. Indeed, fluorescence spectroscopy studies using exogenous fluorophores, such as Photofrin® and aminolevulinic-acid induced protoporphyrin IX, show that there is a significant difference between the measured red fluorescence of the carcinomatous and non-dysplastic tissue as a result of the preferential accumulation of the drug. Initial autoflorescence spectroscopy studies performed at 410 nm excitation report promising results for detecting high-grade dysplasia. However, focal high-grade and low-grade lesions could not be detected reliably. Thus a continuing need exists for further improvements in the optical measurements used to detect early stage carcinomas.

SUMMARY OF THE INVENTION

The present invention relates to a combination of spectroscopic systems that can improve the sensitivity and accuracy of dysplasia detection in patients with BE. Fluorescence, reflectance and light scattering spectroscopies provide complementary information about the biochemical, architectural and morphological state of tissue and the corresponding changes that occur during the progression of dysplasia. A system has been developed providing for combining these three methods to provide for detection, mapping, and/or imaging of tissue. A preferred embodiment of the invention utilizes this trimodal system to guide a biopsy procedure.

Of importance in this system for real time measurements is the simultaneous or near simultaneous collection of light from the same spot or region of interest. The detected diffuse reflectance spectrum is processed to remove a diffusive background component. This is accomplished by measuring a component of the light that is periodic in wavelength. This component arises from the light that is Mie-scattered by surface epithelial cell nuclei, for example. By analyzing the amplitude and frequency of the periodic structure, the density and size distribution of these nuclei can be extracted. For the reflectance, light scattered and fluorescence components to be properly correlated and used to assess a given region of interest, there is preferably substantial overlap of the excitation light for both the reflectance and fluorescence measurements. The reflected light is used to both correct the fluorescence spectrum and to generate a light scattered spectrum based on the use of the periodic structure contained therein. The apparatus delivers both excitation components to the region of interest through the same distal surface of the probe, preferably through the same optical fiber of collection of fibers.

The biopsy channel of an endoscope can be used to insert the fiber optic light delivery and collection system used to obtain measurements. Alternatively, a small diameter endoscope, 5 mm or less in diameter for example, can include the light delivery and collection system suitable for many applications. A preferred embodiment of the system can use a single fiber system for delivery and collection, or alternatively central delivery fiber and six collection fibers concentrically arranged around the delivery fiber. The proximal end of the light delivery and collection probe is optically coupled to both a broadband flash lamp and a monochromatic source such as a laser. A rotating filter or dye wheel can be used to rapidly switch the excitation wavelength over a selected range.

The need for using reflected light arises from the need to correct for the effects of hemoglobin absorption on the measured integrated tissue fluorescence intensity. The combination of fluorescence and reflectance spectroscopies can be applied to remove distortions introduced by scattering and absorption into the entire measured tissue fluorescence spectrum. The undistorted or modified fluorescence spectrum can serve as a sensitive indicator of tissue biochemistry, while reflectance and light scattering spectroscopies provide morphological information on tissue architecture and epithelial cell nuclei. The present invention can include the simultaneous use of all three spectroscopic methods for characterizing tissue and diagnosing disease. The following demonstrates that the combined use of all three techniques provides improved results as compared to the results of each technique individually, in terms of detecting not only high-grade, but also low-grade dysplastic changes in BE, for example.

BRIEF DESCRIPTION OF THE DRAWINGS

FIGS. 3A–3D illustrate fluorescence spectra from non-dysplastic (solid lines), low-grade (dashed-lines) and high-grade dysplastic (dotted lines) (BE) sites. Measured and corresponding extracted intrinsic fluorescence for excitation at 337 nm ((A) and (B)) and 397 nm ((C) and (D)) are shown. Spectra are normalized to their peak intensities. Note the significant lineshape changes. The mean±standard deviation is displayed for each category.

FIG. 10 illustrates relative NADH fluorescence levels as a function of relative collagen fluorescence levels plotted for normal squamous epithelium (squares), benign biopsies (circles) and HSILs (triangles). The three arrows point to the benign biopsies that were classified as "mature squamous epithelium". The remaining benign biopsies were classified as "squamous metaplasia".

FIG. 11A shows reduced scattering coefficient at 400 nm for benign biopsied and high-grade dysplatic sites.

FIG. 11B shows nuclear crowding or total number of nuclei per $mm^2$ plotted as a function of the standard derivation of the nuclear size population for a particular site. Line determined by logistic regression.

Figure 1:
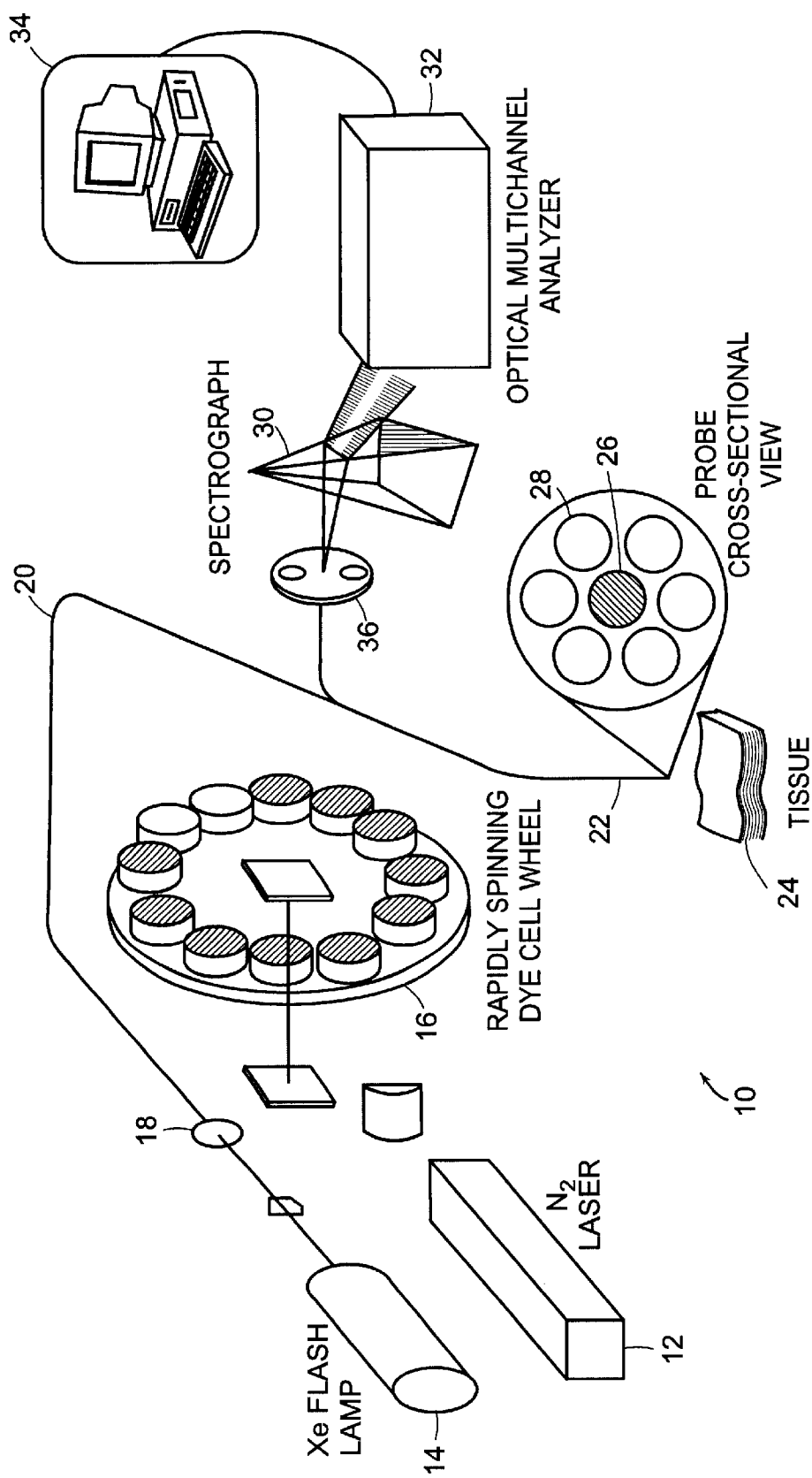
FIG. 1 schematically illustrates a system for performing measurements in accordance with the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Measurements were performed, for example, using a fast excitation-emission matrix (EEM) instrument 10 that has been described in greater detail in U.S. Pat. No. 6,537,211, issued Mar. 25, 2003, the entire contents of which is incorporated herein by reference. The excitation light source of this fast-EEM system can include a nitrogen laser 12 emitting at 337 nm (Laser Science, Inc., Franklin, Mass.; Model: VSL-337MD) pumping 10 dye cuvettes precisely mounted on a rapidly rotating wheel 16. In this manner, eleven different excitation wavelengths were obtained between 337 and 620 nm and coupled using optical system 18 into the delivery fiber of a 1 mm diameter optical fiber probe 20. For the reflectance measurements, white light (350–700 nm) from a Xe flash lamp 14 (Perkin Elmer Opto electronics, Salem, Mass.) was coupled into the same probe. Alternatively, for other embodiments involving measurements in the bladder a XeCl excimer laser emitting at 308 nm can be used. The probe was composed of six collection fibers 28 surrounding the central light delivery fiber 26, and it was covered with a protective, transparent "optical shield" at the distal end 22 as shown in FIG. 1.

During endoscopy, the probe was inserted into the accessory channel of the endoscope and brought into gentle contact with the tissue, thus providing a fixed delivery-collection geometry. The reflected and fluorescence light was collected by the probe and coupled to a spectrograph 30 and detector 22. A second synchronized wheel 36 is used to block the fluorescence excitation wavelength. The average of three sets of spectra from each site was used for analysis using a data processing system 34. Immediately following spectral acquisition, the probe was removed and a slight demarcation remained on the tissue for 30 to 60 seconds as a result of the probe contact. This endoscopically apparent marker was used as a guide for taking a biopsy from the same site at which spectra were acquired. The biopsy specimen was interpreted and classified by a gastrointestinal pathologist. If a dysplastic lesion was suspected, the specimen was reviewed and the diagnosis confirmed by a second gastrointestinal pathologist, in accordance with the standard of care. Data were analyzed from 26 non-dysplastic Barrett's esophagus sites (9 patients), 7 low-grade (4 patients) and 7 high-grade (5 patients) dysplastic sites.

Three types of spectroscopic information were acquired, preferably in less than one second. Fluorescence spectra at eleven different excitation wavelengths, reflectance spectra and light scattering spectra were obtained. Each type of spectrum was analyzed in a manner that provided information about biochemical and morphological changes that occur during dysplastic transformation. Fluorescence spectroscopy can provide valuable information about changes that take place in tissue biochemistry during the development of dysplasia. However, the measured tissue fluorescence spectra can be distorted significantly by unrelated scattering and absorption events. To remove these distortions, the fluorescence spectra were analyzed in combination with information from the corresponding reflectance spectra. The success of this procedure is predicated on the fact that the fluorescence and reflectance spectra collected from a specific site or region of interest using the same light delivery/collection geometry undergo similar distortions. By extracting the intrinsic (undistorted) tissue fluorescence, changes in tissue biochemistry were isolated in a more sensitive and specific manner.

Principal component analysis and logistic regression were employed to determine the correlation between spectral features of the intrinsic fluorescence and histopathological diagnosis. To analyze this relatively small data set in an unbiased manner, "leave-one-out" cross-validation was used. Specifically, the principal components of the intrinsic fluorescence spectra that described the spectral features that change during the progression of dysplasia were selected. The corresponding scores (the coefficients describing the contributions of the principal components to the overall spectra) were used to determine our ability to distinguish (a) high-grade dysplasia from low-grade dysplastic and non-dysplastic BE, and (b) dysplastic (low and high grade) from non-dysplastic BE. To achieve that in an unbiased manner, the following procedure was performed. The scores from a particular site were eliminated, and logistic regression was used to form a decision surface that classified the remaining sites in a manner that optimized agreement with the histopathological classification. The resulting decision surface was then used to classify the excluded site. This process was repeated for each of the sites. This method provided use of a relatively small data set to validate the performance of a decision surface without bias. The decision surface varied minimally during this procedure, indicating the reliability of the technique. Sensitivity and specificity values were determined by comparing the spectroscopic classification with histopathology. Statistical analysis was performed using Matlab statistic software (The Math Works, Inc, Natick, Mass.).

The measured reflectance spectra were analyzed using a representation based on diffusion theory which expressed the reflected light as a function of the absorption ($\mu_a$) and reduced scattering ($\mu_s'$) coefficients of tissue. This analysis provided information about the architecture and morphology of mainly the connective tissue, i.e. the lamina propria and the submucosa, as the collected light originated within 500–700 $\mu$m from the tissue surface. The diagnostic value of the resulting tissue scattering coefficient values was determined by correlating the results of logistic regression and cross-validation with histopathological classification, as in the intrinsic fluorescence case.

A small fraction (2–5%) of the detected reflected light originated from light collected by the probe after being scattered only once by the tissue. This method described generally herein as light scattering spectroscopy is described in greater detail in U.S. Pat. No. 6,091,984, issued on Jul. 18, 2000, the entire contents of which is incorporated herein by reference. Additional methods for measuring tissue structure are described in International Application No. PCT/US98/21450, filed on Oct. 9, 1998, now Publication No. WO99/18845, the entire contents of which is also incorporated herein by reference. The intensity of this singly-scattered light contained a component which was periodic in inverse wavelength, the magnitude and frequency of which depended on the number and size of the nuclei in the epithelial cell layer. This periodic signal was analyzed to determine the number and size of epithelial cell nuclei corresponding to a particular site. Logistic regression and cross-validation were then use to compare the spectroscopic classification with that of histopathology. To optimize sensitivity and specificity, the posterior probability threshold for separating high-grade dysplasia from non-high-grade dysplasia sites was set to 0.3 in one example.

Finally, results from all three spectroscopic techniques were combined to determine whether the number of correctly classified sites can be improved. Specifically, a site was assigned a classification that was consistent with results from at least two of the three analysis methods, and this classification was compared to histopathology.

Figure 2B:
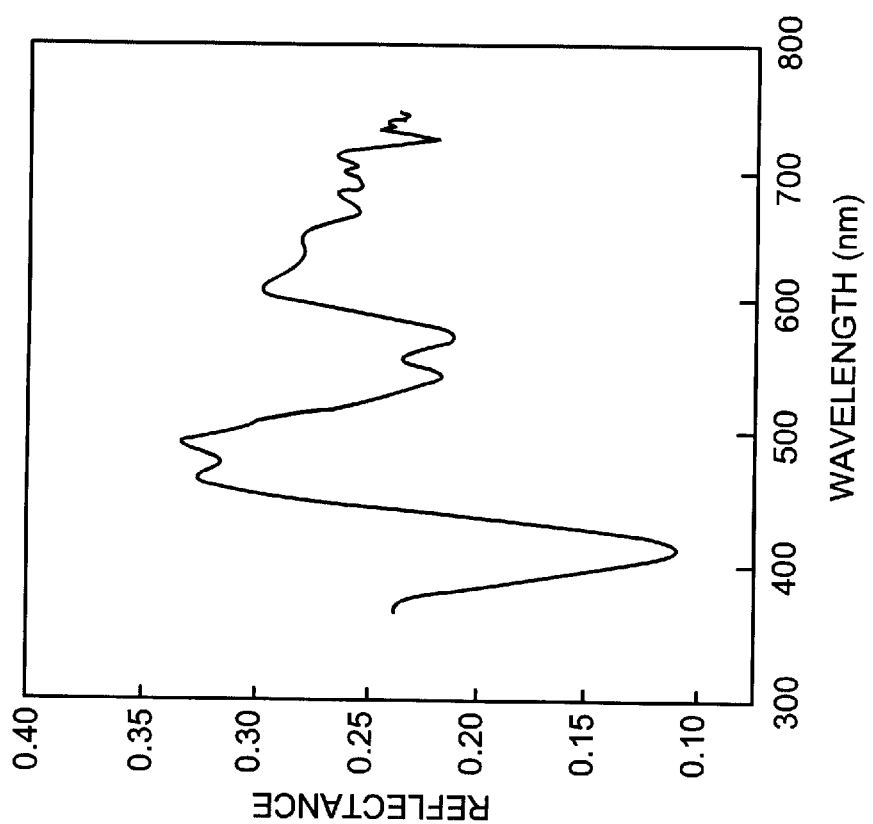
FIG. 2B is a corresponding reflectance spectrum.
Figure 2A:
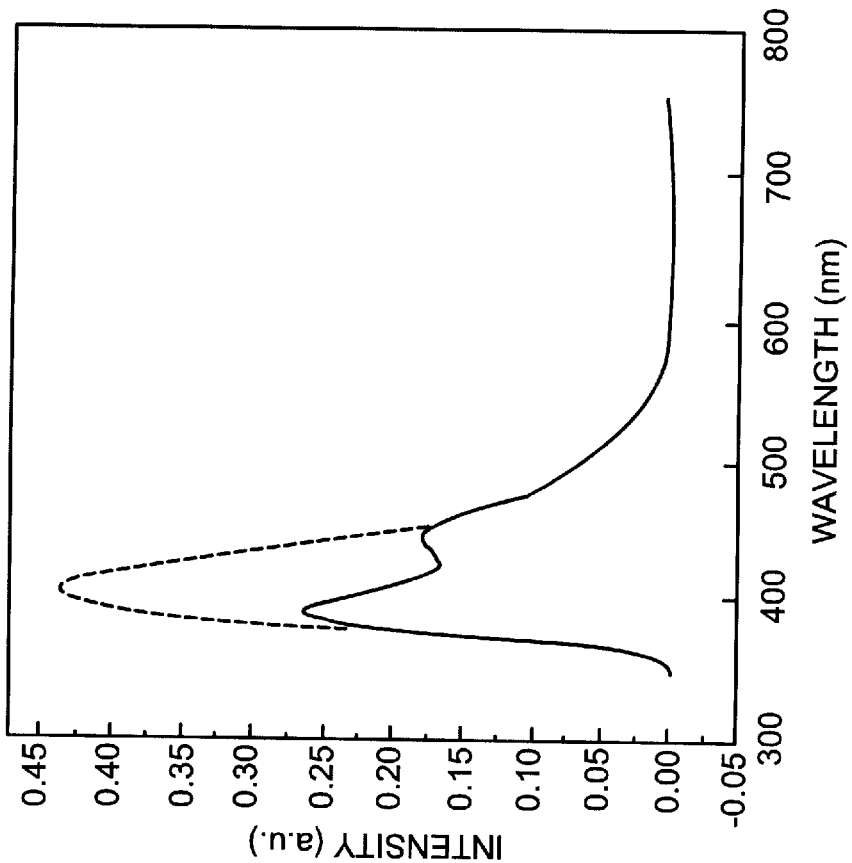
FIG. 2A illustrates fluorescence from a non-dysplastic Barrett's esophagus site, 337 nm excitation. Measured spectrum, solid line; extracted intrinsic fluorescence dashed line.

FIG. 2A shows a typical fluorescence spectrum excited with 337 nm light from a non-dysplastic BE site (solid line). There are two peaks, which can be attributed to the presence of two different tissue fluorophores. Note that the fluorescence intensity decrease between these two peaks occurs at the wavelength range in which hemoglobin absorbs light very efficiently. The effects of hemoglobin absorption are clearly observed in the corresponding reflectance spectrum, which exhibits minima at approximately 420, 540 and 580 nm, corresponding to oxy-hemoglobin absorption peaks (FIG. 2B). When the measured fluorescence spectrum of FIG. 2A is processed in combination with the corresponding reflectance spectrum of FIG. 2B as discussed herein, the intrinsic (undistorted) tissue fluorescence spectrum at the particular excitation wavelength is obtained (FIG. 2A, dashed line). Note that this spectrum consists of a single broad peak.

Figure 3B:
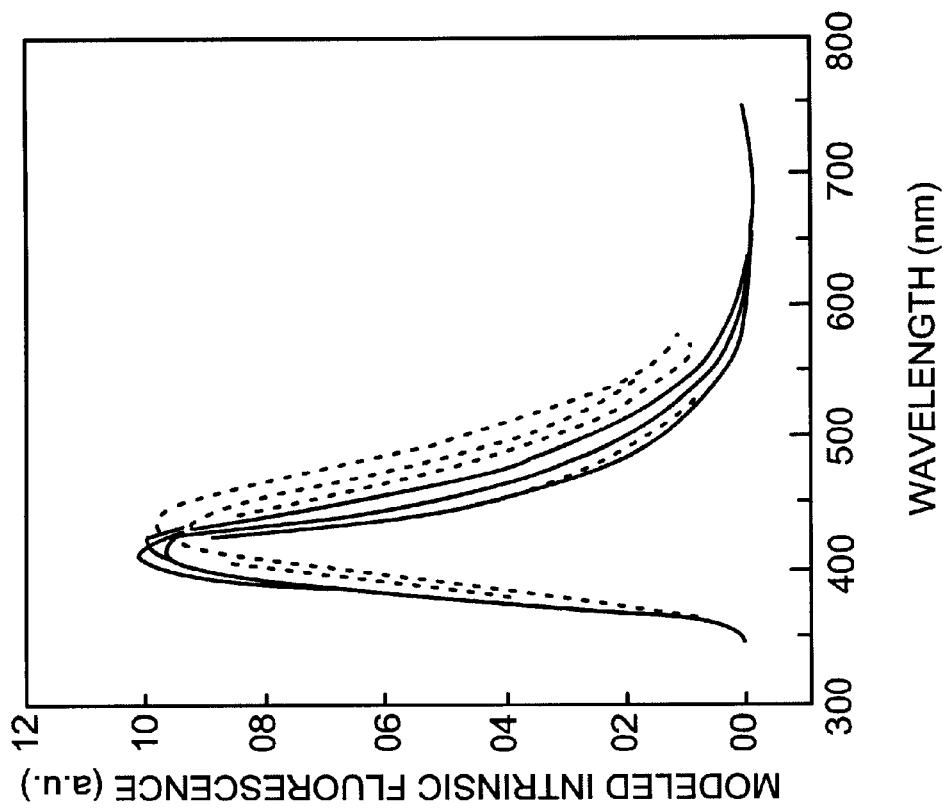
Figure 3A:
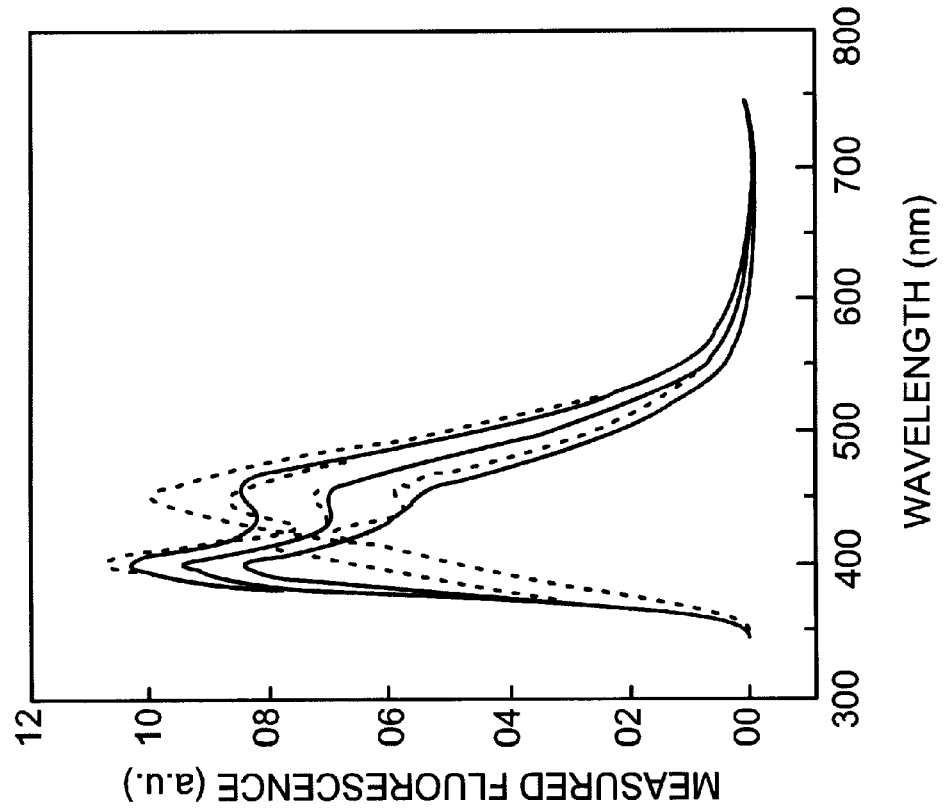

Significant differences are observed in the representation of intrinsic tissue fluorescence of non-dysplastic and dysplastic BE sites excited at 337 nm (FIGS. 3A and 3B) and 397 nm (FIGS. 3C, 3D). At 337 nm excitation the lineshape of the dysplastic sites broadens and shifts to the red region of the spectrum during the progression from non-dysplastic, to low-grade, to high-grade dysplasia. At 397 nm excitation, the fluorescence increases in the red region of the spectrum for the dysplastic BE sites. Similar changes are observed at 412 nm excitation.

Figure 4:
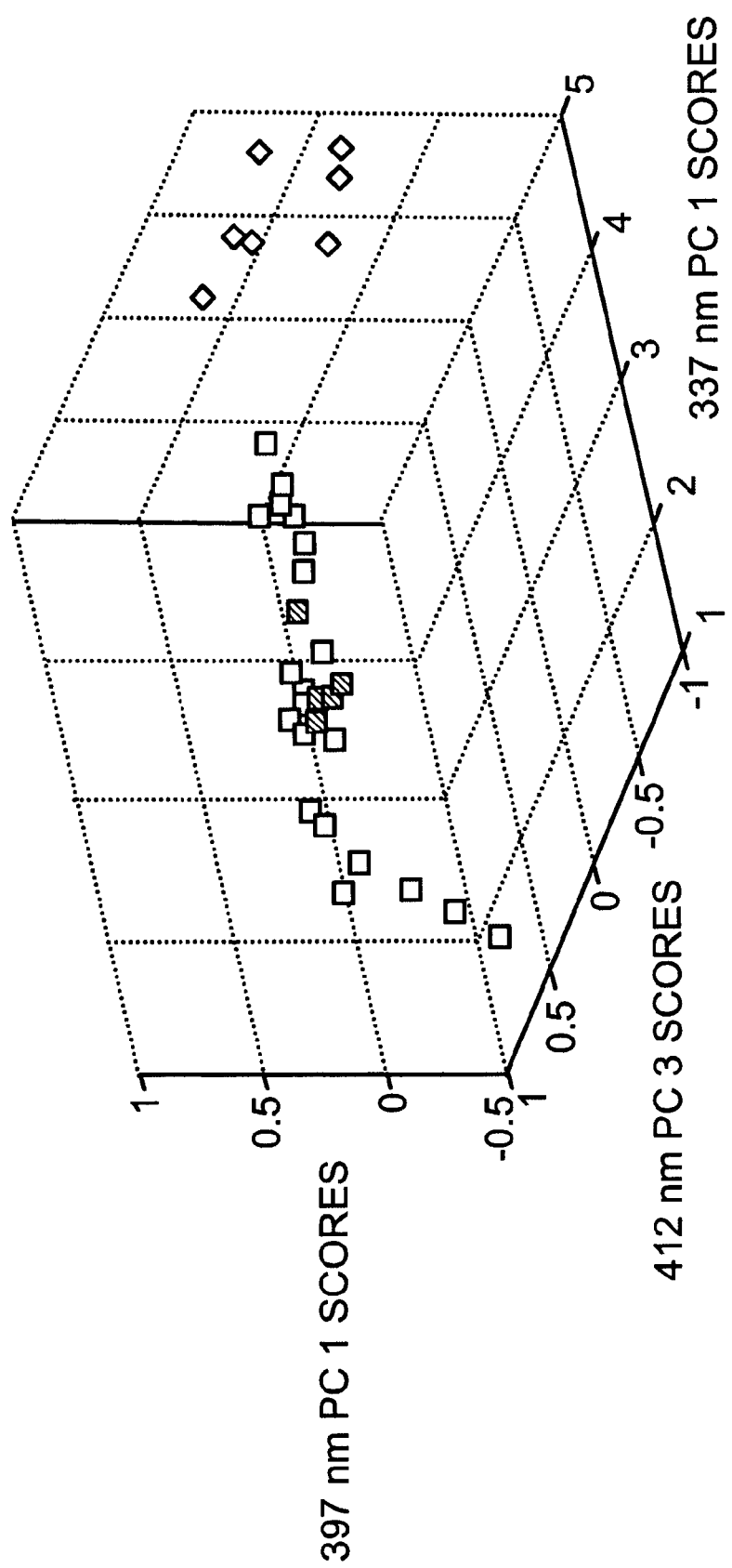
FIG. 4 illustrates scores of three principal components extracted from decomposition of intrinsic fluorescence spectra at 337, 397 and 412 nm excitation used to distinguish high-grade dysplasia (diamonds) from non-dysplastic and low-grade dysplasia (squares) (BE) sites. At 337 nm excitation, decomposition was performed in the 460 to 520 nm region of the intrinsic fluorescence spectra, as this is the wavelength range within which spectral differences are most pronounced. Similarly, at 397 nm excitation principal components were extracted from the intrinsic fluorescence spectra between 600 and 650 nm. PC1 indicates the first principal component and PC3 the third.
Figure 5:
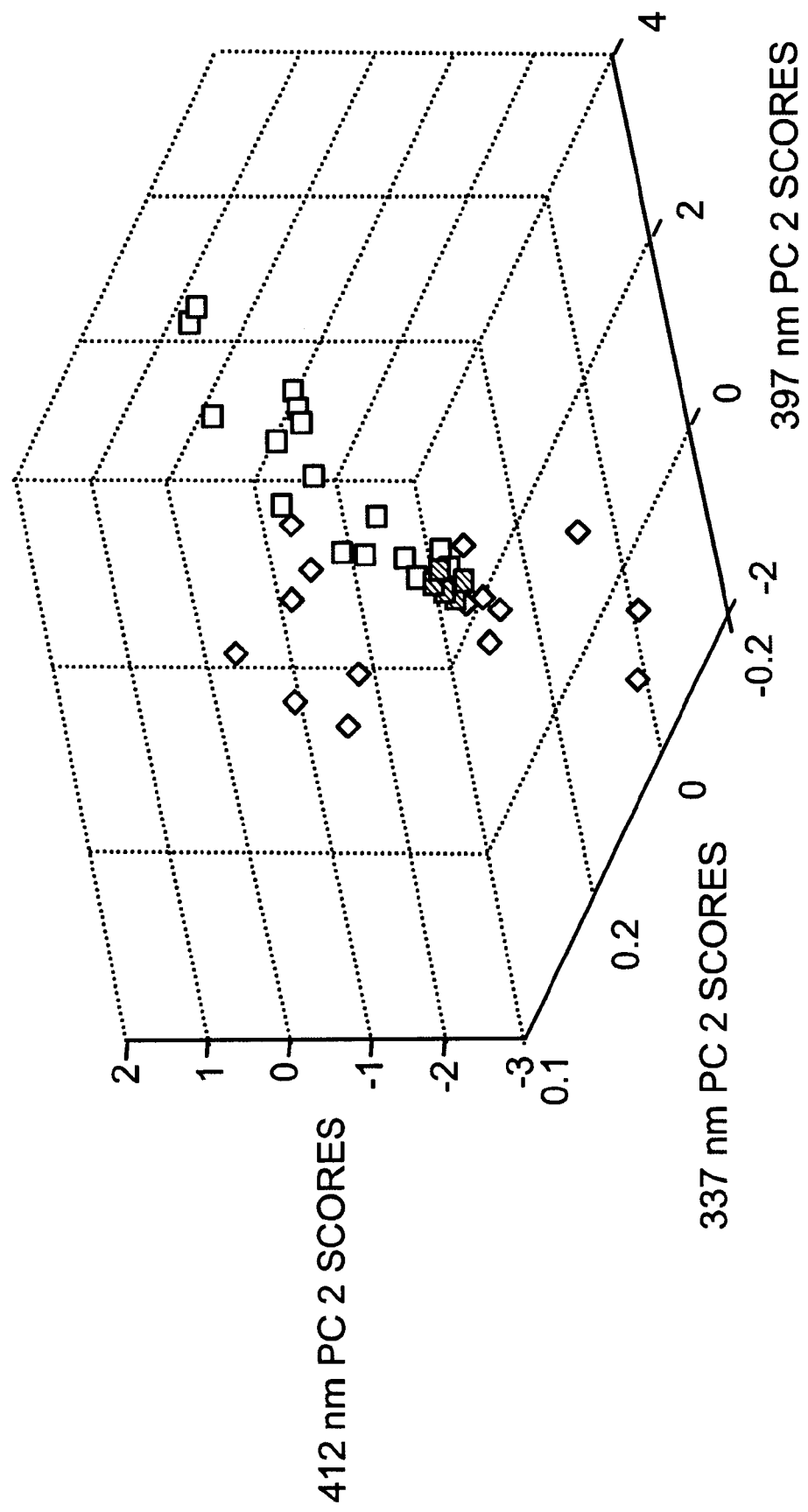
FIG. 5 illustrates scores of three principal components extracted from decomposition of the entire intrinsic fluorescence spectra at 337, 397 and 412 nm excitation used to distinguish dysplastic (low- and high-grade; diamonds) from non-dysplastic (squares) (BE) sites. PC2 indicates the second principal component.

These differences can be used to develop algorithms for detecting dysplasia in BE. Specifically, principal component analysis, logistic regression and leave-one-out cross-validation are employed to determine the sensitivity and specificity with which we can separate (a) non-dysplastic from dysplastic (low and high-grade) tissue, and (b) high-grade dysplasia from low-grade and non-dysplastic BE epithelium. In each case, the scores of one of the first three principal components extracted from the intrinsic fluorescence spectra at 337, 397, and 412 nm excitation are used (FIGS. 4 and 5). The selected principal components describe the observed spectral differences. From this analysis, sites with high-grade dysplasia can be differentiated from low-grade and non-dysplastic sites with high sensitivity and specificity (Table 1). Additionally, dysplastic and non-dysplastic epithelia can be distinguished with very high sensitivity and specificity.

Table 1 illustrates the accuracy of spectroscopic classification of non-dysplastic (NDB), low-grade (LGD) and high-grade dysplastic (HGD) tissue in Barrett's esophagus.

|  | HGD vs (LGD and NDB) | | (LGD and HGD) vs NDB | |
| --- | --- | --- | --- | --- |
|  | Sensitivity | Specificity | Sensitivity | Specificity |
| Intrinsic fluorescence (IF) | 100% | 98% | 71% | 92% |
| Reflectance (R) | 86% | 100% | 79% | 88% |
| Light Scattering (LS) | 100% | 91% | 93% | 96% |
| Combination of IF, R and LS | 100% | 100% | 93% | 100% |

Figure 6:
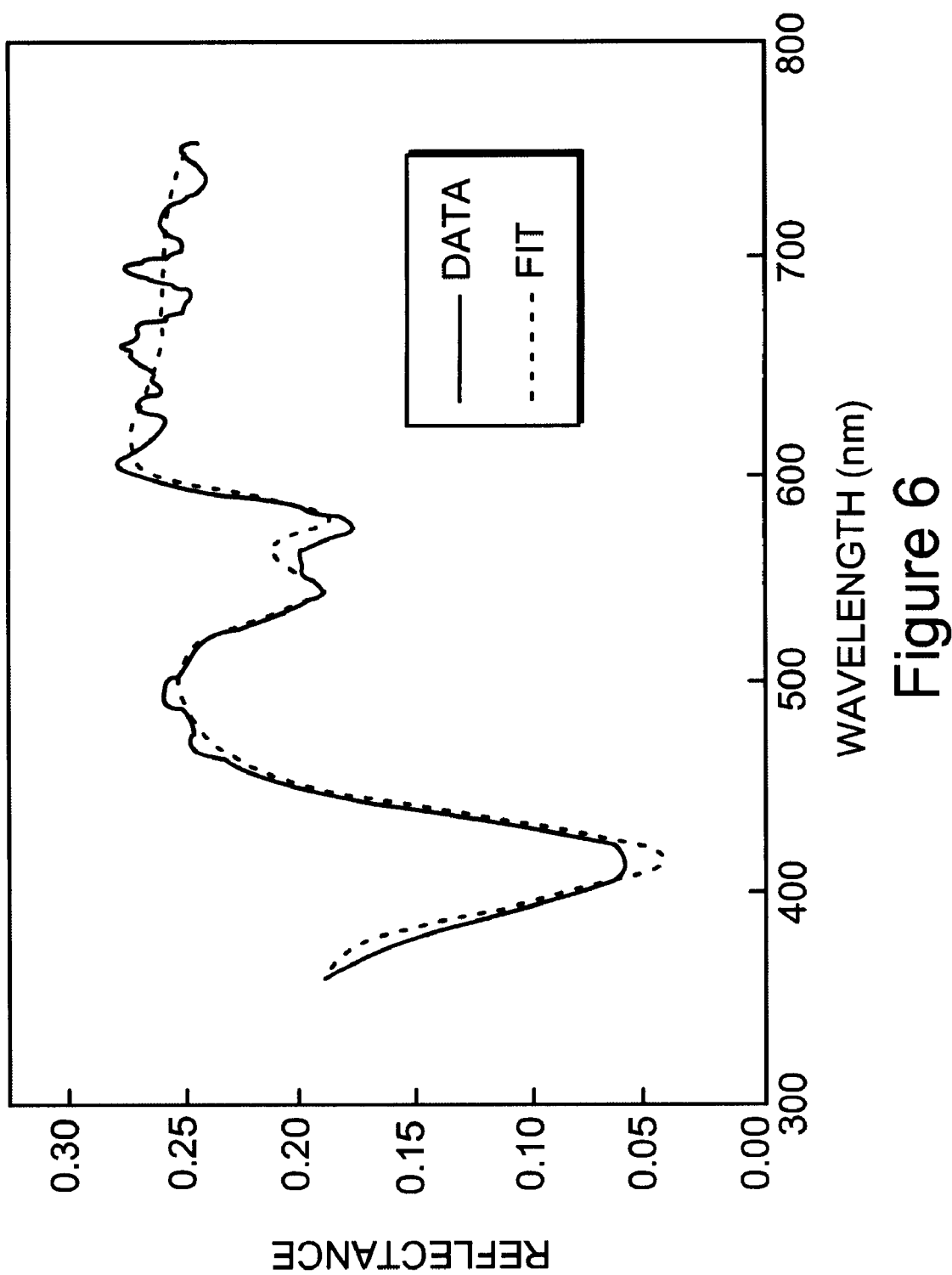
FIG. 6 is a reflectance spectrum of a non-dysplastic Barrett's esophagus site. Solid line represents the measured data and the dashed line represents the projected properties of the tissue based on known scattering and absorption properties of the tissue.

Reflectance spectra can be analyzed using a mathematical representation to obtain detailed information about the scattering and absorption properties of the bulk tissue. A typical reflectance spectrum with the corresponding fit obtained using this representation is shown in FIG. 6.

Figure 7:
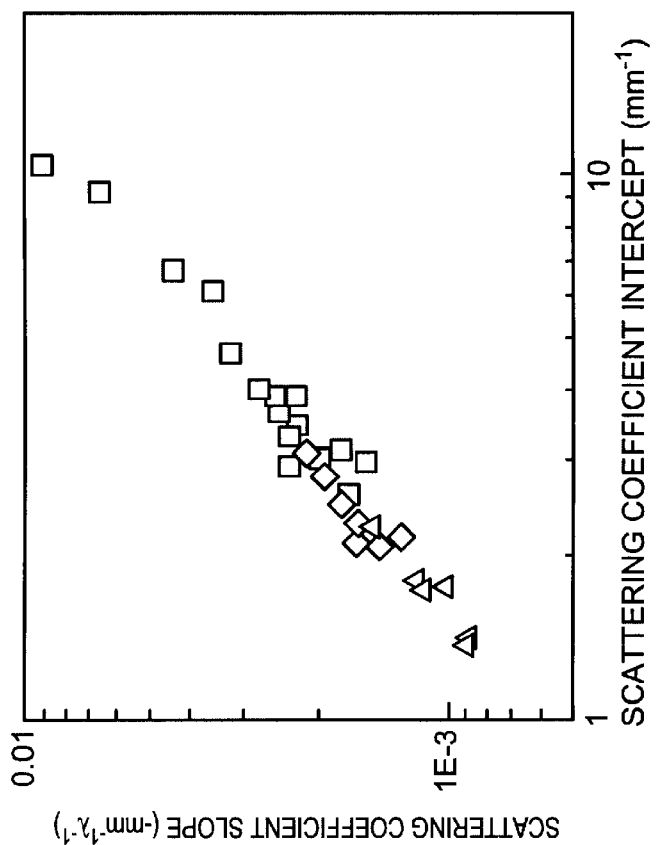
FIG. 7 illustrates the slopes and intercepts of wavelength dependent tissue reduced scattering coefficient, $\mu_s'$, for non-dysplastic (squares), low-grade (diamonds) and high-grade (triangles) dysplastic (BE) sites. In each case, a straight line was fit to $\mu_s'(\lambda)$, extracted from the reflectance spectrum. A log—log scale is used to facilitate visualization of all the data points.
Figure 9B:
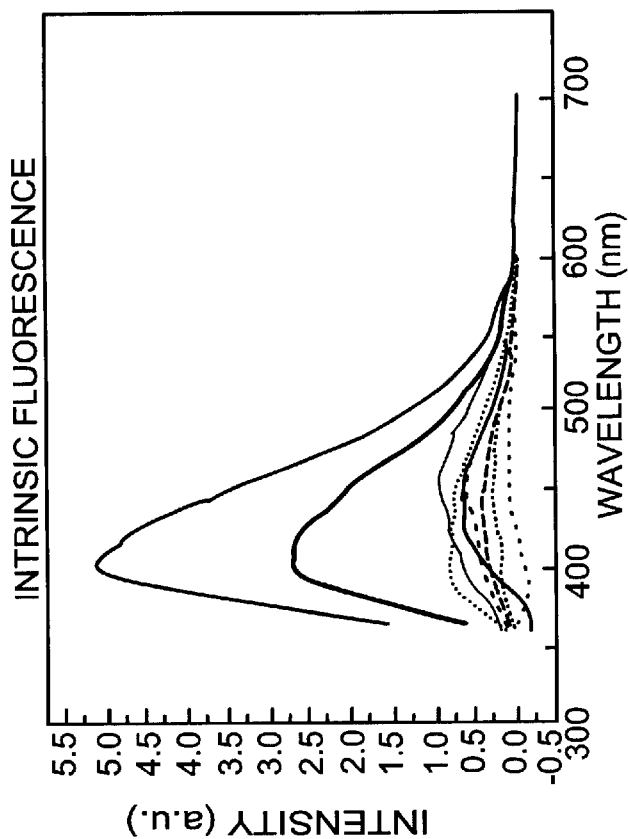
FIGS. 9A–9D illustrate measured and intrinsic fluorescence spectra of normal squamous epithelium (solid line), benign biopsied sites (dashed lines) and high-grade SILs (dotted lines). Curves A and B show differences in the lineshape and intensity observed at 337 nm excitation. Curves C and D show intensity differences observed in the intrinsic fluorescence excited at 358 nm.
Figure 9A:
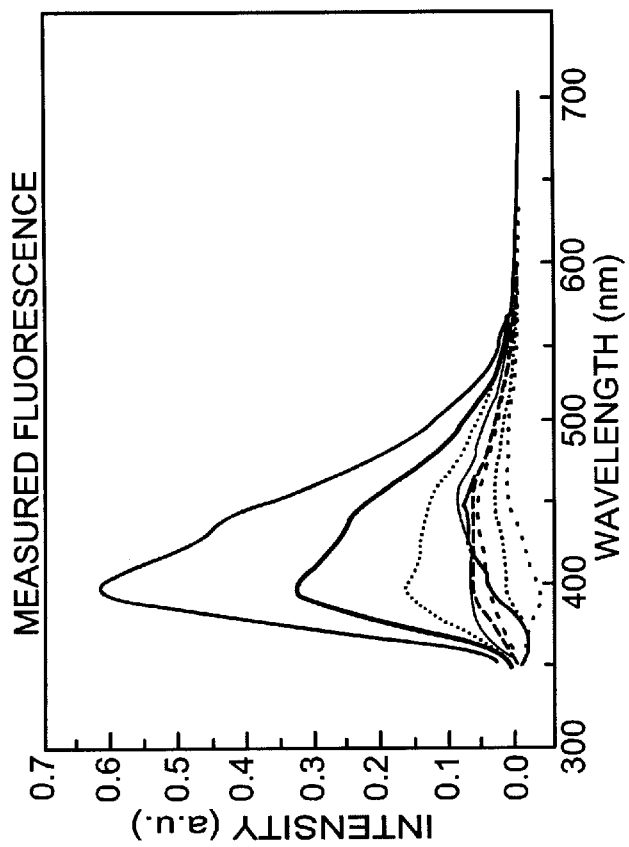
Figure 9D:
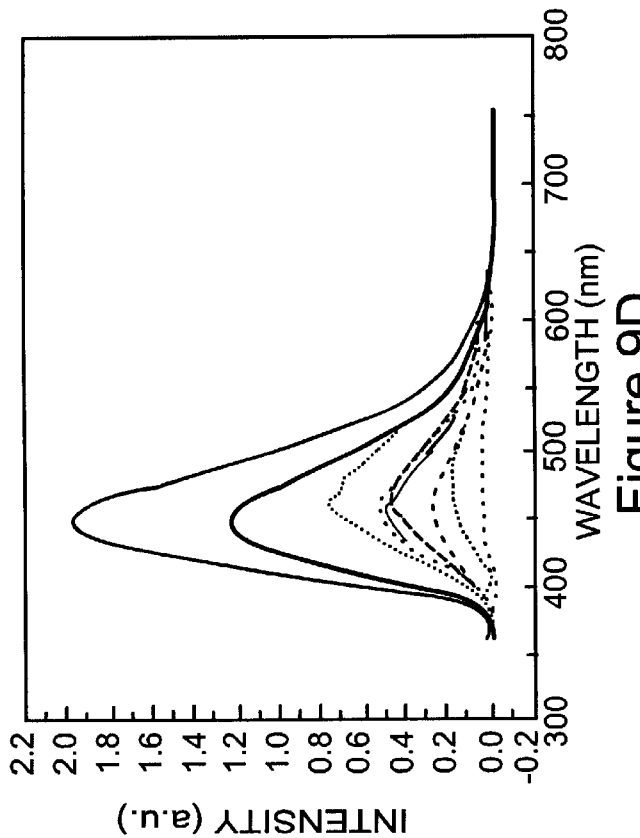
Figure 9C:
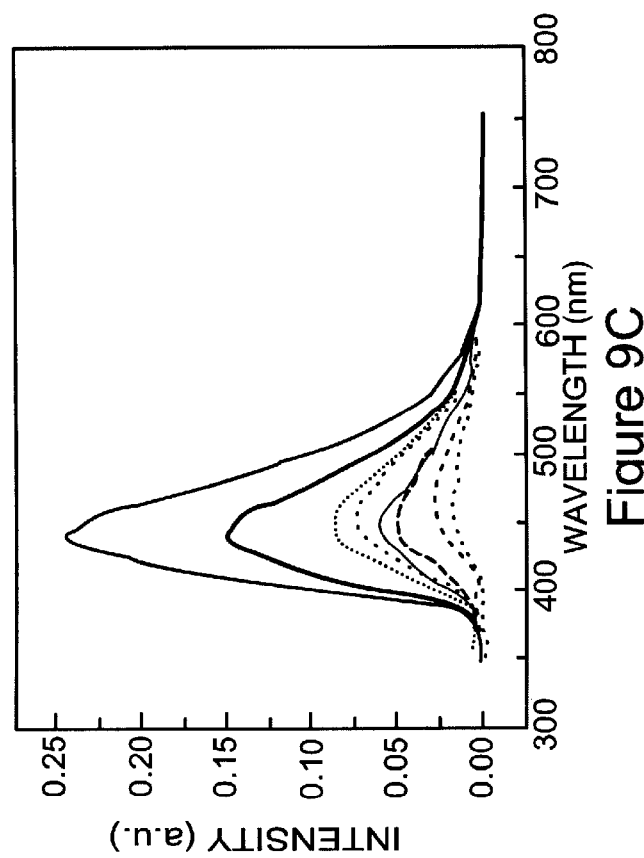

This type of analysis shows that the reduced scattering coefficient $\mu_s'$ of Barrett's esophagus tissue changes gradually during the progression from non-dysplastic, to low-grade, to high-grade dysplasia. For example, at 400 nm the $\mu_s'$ of high-grade dysplastic tissue (1.3±0.2 mm$^{-1}$) is lower than that of low-grade dysplastic tissue (1.8±0.3 mm$^{-1}$) which, in turn, is lower than that of non-dysplastic BE tissue (3±1.6 mm$^{-1}$). Additionally, the wavelength dependence of $\mu_s'$ changes during the development of dysplasia. To describe these changes, a straight line is fit to $\mu_s'(\lambda)$ and the intercept and slope of this line are used as diagnostic parameters (FIG. 7). Using logistic regression and leave-one-out cross-validation, the sensitivity and specificity for classifying tissue in accordance with histopathology are determined. This method results in slightly lower overall sensitivity and specificity values than those achieved with the intrinsic fluorescence spectra (Table 1).

Figure 8:
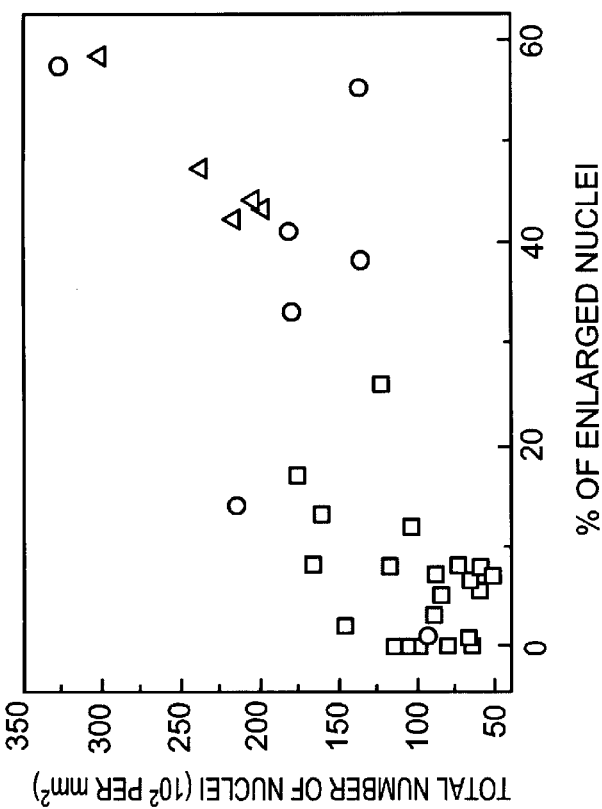
FIG. 8 illustrates the total number of nuclei per $mm^2$ plotted as a function of percentage of enlarged nuclei (diameter>10 $\mu$m), as determined from the light-scattering model analysis. Non-dysplastic Barrett's are represented by squares, low-grade dysplasia are represented by circles; and high-grade dysplasia are represented by triangles.

The reflectance spectra are further processed in a manner that allows extraction and analysis of the backscattered light from the epithelial cell nuclei. The results of this analysis are displayed in FIG. 8. The ordinate of FIG. 8 represents the number of nuclei per square mm, indicative of the degree of nuclear crowding, and the abscissa represents the percentage of enlarged nuclei, defined as nuclei having diameter greater than 10 microns. Note that the non-dysplastic samples are concentrated in the lower left-hand corner, indicating cell nuclei that are small and free of crowding. As dysplasia progresses, the data points move to the upper right, indicating nuclear enlargement and crowding, in agreement with the findings of histopathology. This technique is superior in terms of separating the dysplastic (low and high-grade) from the non-dysplastic BE sites (Table 1).

The ability to characterize dysplastic and non-dysplastic tissue in BE is improved by combining the information provided by each one of the spectroscopic techniques, obtained simultaneously with the system. When a spectroscopic classification is consistent with at least two of the three analysis methods, high-grade dysplasia is identified with perfect sensitivity and specificity, and dysplastic tissue is distinguished from non-dysplastic tissue with perfect specificity, while maintaining very high sensitivity (Table 1).

Spectroscopic techniques use information contained in light signals to assess the state of biological tissue. Optical fiber technology allows spectroscopy to be applied as a diagnostic tool for a wide range of tissues that are accessible endoscopically. The use of spectroscopy as described herein can be used for improving the physician's ability to detect pre-cancerous (dysplastic) and early cancerous lesions in many organs, such as the oral cavity, the cervix, the lung, the breast and the gastrointestinal tract. Depending on the technique employed, specific information can be acquired about tissue biochemical, architectural and morphological features. Microscopic changes in these features that occur during the progression of dysplasia may be detectable spectroscopically before the manifestation of macroscopic changes that are visible endoscopically. Additionally, spectroscopic techniques are non-invasive, allowing study of the tissue in its native state, free of artifacts introduced by cutting and chemically processing the tissue. In principle, spectroscopic signals can be analyzed in real time, thus guiding the physician to biopsy areas that are likely to yield significant pathology or possibly allowing her to make an immediate decision on the type of intervention that is required for successful treatment of the patient. Furthermore, the spectroscopic signals carried by light can be used as objective guides for assessing a particular tissue site, especially in areas in which the intra- and inter-observer agreement on the classification of disease is not very good.

The targets of fluorescence spectroscopy include tissue biochemicals such as NADH, FAD, collagen, elastin and porphyrins. Exogenous or exogenously-induced chromophores that have been shown to accumulate preferentially in the diseased areas can also be used. The detection of high-grade dysplasia using tissue autofluorescence excited at 410 nm have been conducted. The difference between the measured integrated intensity-normalized fluorescence and the mean normalized fluorescence from normal esophageal tissue was used for the diagnostic procedure. The main spectral features that resulted in good differentiation between high-grade dysplastic and non-dysplastic tissues were the presence of decreased fluorescence around 470–480 nm and increased fluorescence in the red region of the spectrum for the high-grade dysplastic tissues. However, this process does not classify correctly sites with low-grade or focal high-grade dysplasia.

In the present example illustrating an embodiment of the invention, fluorescence spectra at 11 different excitation wavelengths between 337 and 610 nm were obtained. Thus, instead of a single fluorescence spectrum an excitation-emission matrix (EEM) is collected. EEMs can be used to identify the excitation wavelengths at which tissue classification is optimized. Additionally, EEMs can assist in identifying the origins of the measured fluorescence signals in a more reliable manner. Nevertheless, as shown in FIGS. 2 and 3, these measured EEMs can be distorted significantly by tissue scattering and absorption. To eliminate artifacts introduced by changes in scattering or absorption, rather than by tissue biochemistry, corresponding reflectance spectra can be used which are affected in a similar manner by scattering and absorption events. Once the distorted measured tissue fluorescence spectra are rectified using the reflectance, tissue fluorescence excited at 337 nm broadens and shifts to longer wavelengths in a very consistent manner as the tissue progresses from non-dysplastic to low-grade to high-grade dysplasia (FIG. 3). These spectral changes are consistent with the presence of increased NADH levels in dysplastic tissue. Our findings at 397 and 412 nm excitation are attributed to endogenous porphyrins. The spectra corresponding to the high-grade dysplasia sites appear slightly distorted around 470 nm, even after correcting for the effects of scattering and absorption. This suggests that this difference arises as a result of biochemical changes rather than absorption changes.

To demonstrate the level of significant changes that are observed in tissue fluorescence during the development of dysplasia, we use the scores of one of the first three principal components which described over 99% of the variance observed in the intrinsic fluorescence spectra excited at 337, 397 and 412 nm. Subsequently, we use logistic regression and leave-one-out cross-validation to estimate and validate in an unbiased manner the sensitivity and specificity with which we can distinguish (a) high-grade dysplasia from low-grade and non-dysplastic tissue, and (b) dysplastic (low and high-grade) from non-dysplastic tissue to separate high-grade dysplasia from low-grade and non-dysplastic tissue, spectroscopic classification is consistent with histopathology in all but one case. Additionally, we can distinguish dysplastic from non-dysplastic tissue with very high sensitivity and specificity.

Reflectance spectroscopy can be used not only to remove the distortions observed in the measured tissue fluorescence spectra, but also to provide very detailed and potentially useful information about morphological and architectural features of the tissue. Specifically, as shown in FIG. 6 the observed tissue reflectance spectra can be used in terms of two parameters that are determined by tissue scattering and absorption. For example, changes in the concentration or the oxygen saturation of hemoglobin, the main absorber in the visible spectrum for this tissue type, result in concomitant changes in the absorption coefficient of tissue. Alterations in the architecture of the connective tissue collagen fibers, one of the main contributors of tissue scattering, will lead to a modified tissue scattering coefficient. Indeed, analysis suggests that the scattering coefficient of tissue decreases significantly during the development of dysplasia, suggesting that changes that are not observed histopathologically are taking place within the lamina propria and submucosa before the onset of invasion. Recently, it has been shown that an increased level of cysteine and serine proteases is found in gastric and colorectal cancerous and precancerous lesions. The findings related to the decrease in the value of the scattering coefficient during the progression of dysplasia are consistent with the presence of such enzymes, which could result in a less dense collagen matrix, for instance. The change in the slope of $\mu_s'$ as a function of wavelength suggests that the mean size of the tissue scattering particles is changing. Crowding of the cells and nuclei of the epithelial layer may be responsible for this change. As shown in Table 1, one can use the observed changes in tissue scattering to classify tissue quite successfully.

Light scattering spectroscopy is a procedure that can be used to obtain information about the number and the size of nuclei of the epithelial cell layer. Epithelial cell nuclei are the primary targets of reflected light that is singly scattered before it is collected by a probe of the preferred embodiment. The intensity and oscillations of this singly-backscattered light are characteristic of the number and size of its target nuclei. This technique is used to characterize pre-cancerous and early cancerous changes in the colon, the oral cavity, the bladder and (BE). We include the results of this technique for the data set of this particular study to illustrate the information that can be acquired and combined with fluorescence and reflectance spectroscopies. We find that light scattering spectroscopy outperforms the other two methods in terms of its ability to separate the dysplastic from non-dysplastic BE sites.

The combination of all three techniques provides an extremely sensitive and specific tool for the detection of dysplasia in BE. In this case, agreement with histopathology is achieved in terms of separating high-grade dysplasia from non-dysplastic and low-grade dysplasia sites. Additionally, all sites are classified correctly as dysplastic or non-dysplastic, with the exception of one site. The observed improvement is expected, since each one of the techniques examines different features of tissue biochemistry and morphology that can be altered during the development of dysplastic changes.

Pancreatic carcinoma is one of the first five leading causes of death in Western countries and has a very poor prognosis after initial diagnosis. This is due to late presentation of symptoms and the fact that only about 5–20% of all patients are eligible for resection. Adenocarcinoma of the pancreas arises from the ductal epithelium. In the precancerous stages ductal epithelial cells undergo morphological changes similar to those of BE including increasing nuclear size and crowding. Several clinical conditions exist which may allow detection of precancerous or early cancerous changes. These include acute or chronic pancreatitis due to focal obstruction of the pancreatic duct, acute pancreatitis due to intraductal papillary mucinous tumor of the pancreas (IPMT), and patients with a strong family history of pancreatic cancer. Detection of dysplasia in this setting is currently based on the detection of stricturing or dilation of the pancreatic duct, and exfoliative cytology. However, these methods cannot reliably distinguish dysplasia and inflammation and have an overall poor sensitivity of 44–70%.

The present invention includes methods for performing trimodal spectroscopic analysis within the main pancreatic duct using the technique of endoscopic retrograde cholangio-pancreatography (ERCP), and obtained spectra from the pancreatic duct epithelium.

The majority of patients with ductal adenocarcinoma of the pancreas present with late stage tumors that are not amenable to curative therapy. A significant minority of patients present for evaluation at a time where early dysplasia of carcinomas are detectable. These include strictures of the main pancreatic duct (MPD), and IPMT presenting as acute pancreatitis, and in patients with a strong family history of carcinoma of the pancreas. In all of these cases, the presence of dysplasia, and the distribution of dysplasia along the length of the pancreas are critical to management decisions (whether to remove part of all of the pancreas). The present invention can be directed to the use of tri-modal spectroscopy for the detection of dysplasia an invasive cancer in the pancreatic duct. The present invention can evaluate ex vivo or in vivo specimens of patients to detect pancreatic cancer of dysplasia. Spectra can be collected from the MPD at 1 cm intervals within 3 hours of resection and before formalin fixation. Trimodal spectral analysis can be performed to evaluate for components which accurately discriminate histological categories. These spectral algorithms can be applied in vivo to patients undergoing endoscopic retrograde cholangiopancreatography for evaluation of the 3 conditions mentioned above. Spectra can be collected in vivo at 1 cm intervals along with entire length of the duct. Spectral signals can be compared to histology among the patients whose clinical condition dictates surgical removal of the pancreas. Anatomic locations of the spectral signals can be matched according to the distance from MPD orifice.

The present invention can be employed for the detection of preinvasive disease of the cervix either alone or at the time of colposcopy following an abnormal Pap smear. The present invention can also be used for a non-invasive method of monitoring the progress of medical therapies for preinvasive disease.

The Pap smear is a screening tool for cervical tissue abnormalities. Abnormal Pap smears are routinely followed up by colposcopy. This process uses a low-power binocular microscope for the identification of abnormal cervical epithelium, which is subsequently biopsied and examined histopathologically. It is estimated that in expert hands the sensitivity and specificity of colposcopy are 94% and 48%, respectively.

A preferred embodiment of the present invention include spectroscopic techniques to evaluate cervical epithelium in vivo. Tissue fluorescence spectra excited at 337, 380 and 460 nm were acquired during colposcopy from normal and suspicious sites within the ectocervical and endocervical regions. Suspicious sites were biopsied and classified histopathologically. An initial set of spectra was analyzed and statistical methods were developed to optimize the agreement between spectroscopic and histopathological classification. When these methods were used prospectively to classify a second set of data, it was found that squamous intraepithelial lesions (SILs) can be identified spectroscopically with 82% sensitivity and 68% specificity when compared to histopathology. The present invention improves upon the sensitivity and specificity of spectral analysis of cervical epithelium in a real-time in vivo approach. The method employs trimodal spectroscopy (TMS), the combined use of intrinsic fluorescence spectroscopy (IFS), diffuse reflectance spectroscopy (DRS), and light scattering spectroscopy (LSS).

The method can compare the spectra obtained using trimodal analyser with the histologic diagnosis of the area of epithelium biopsied. This process provides patterns that are predictive of histologic dysplasia in a prospective fashion, thus allowing the clinician to increase the positive histologic lesions of the cervical epithelium prospectively. This can be of immense value in following patients on clinical trials in order to determine the response to medical treatments of cervical dysplasia.

Spectra can be acquired from the normal squamous ectocervix and suspicious sites within the transformation zone. The latter were biopsied immediately following spectral acquisition. Data were collected from 34 patients, 42 normal ectocervical sites (not biopsied), 15 benign biopsied sites (12 classified as squamous metaplasia and 3 as mature squamous epithelium) and 10 high-grade squamous intraepithelial lesions (HSILs).

Differences in the intrinsic fluorescence intensity and/or lineshape were observed for several excitation wavelengths as shown in FIGS. 9A–9D.

Instead of using principal component analysis for the assessment of the diagnostic potential of intrinsic fluorescence spectroscopy, the spectra were decomposed as a linear combination of the NADH and collagen EEMs extracted from the measurements performed during variceal ligation.

A significant decrease was observed in collagen fluorescence of the benign biopsied sites and HSILs compared to that of the normal squamous epithelium as seen in FIG. 10. These changes result from differences in the levels of expression of matrix metalloproteinases (MMPs), a class of enzymes responsible for collagen degradation. Differences in the levels and/or patterns of expression of MMP-2 have been reported between normal squamous epithelium, squamous metaplasia and SILs. Additionally, an increase in the NADH fluorescence is noted for the HSILs compared to that of benign biopsied sites as seen in FIG. 11A. This increase could be the result of an increase in the number of epithelial cells and/or their metabolic activity (52). Using logistic regression and "leave-one-out" cross-validation, as in the case of Barrett's esophagus, we found that we could distinguish the HSILs from the benign biopsied sites with a sensitivity of 80% and a specificity of 67%.

Analysis of the diffuse reflectance spectra using the periodic component in the scattered light indicated that the reduced scattering coefficient of the HSILs was generally lower than that of the squamous metaplastic and mature squamous epithelium biopsied sites as seen in FIG. 11B. When the value of $\mu_s'$ at 400 nm was used to perform logistic regression and cross-validation, 7/10 HSILs (70% sensitivity) and 9/15 benign biopsied sites (60% specificity) were classified correctly.

Extraction and analysis of the light scattering spectra indicated that the variation in nuclear size, i.e. the standard deviation of the nuclear size population corresponding to a particular site, had a higher diagnostic value than the percentage of enlarged nuclei considered in the case of Barrett's esophagus. Using logistic regression and cross validation with the nuclear size standard deviation and the number of nuclei per unit area as diagnostic parameters, we found that we could separate HSILs from the benign biopsied sites with 90% sensitivity and 67% specificity as seen in FIG. 11B.

Finally, we combined the three techniques, IFS, DRS and LSS, in a manner that classified a particular site according to the diagnosis that was consistent with at least two of the three methods of analysis. This simple approach led to superior sensitivity and specificity (100% and 80%, respectively) for the detection of HSILs from non-HSIL sites biopsied within the transformation zone when compared to any one of the techniques alone as seen in Table 2.

TABLE 2

| | benign biopsies vs HSIL | |
|---|---|---|
| | Sensitivity | Specificity |
| Intrinsic Fluorescence Spectroscopy (IFS) | 80% | 67% |
| Diffuse Reflectance Spectroscopy (DRS) | 70% | 60% |
| Light Scattering Spectroscopy (LSS) | 90% | 67% |
| Tri-Modal Spectroscopy (TMS) | 100% | 80% |

Figure 12:
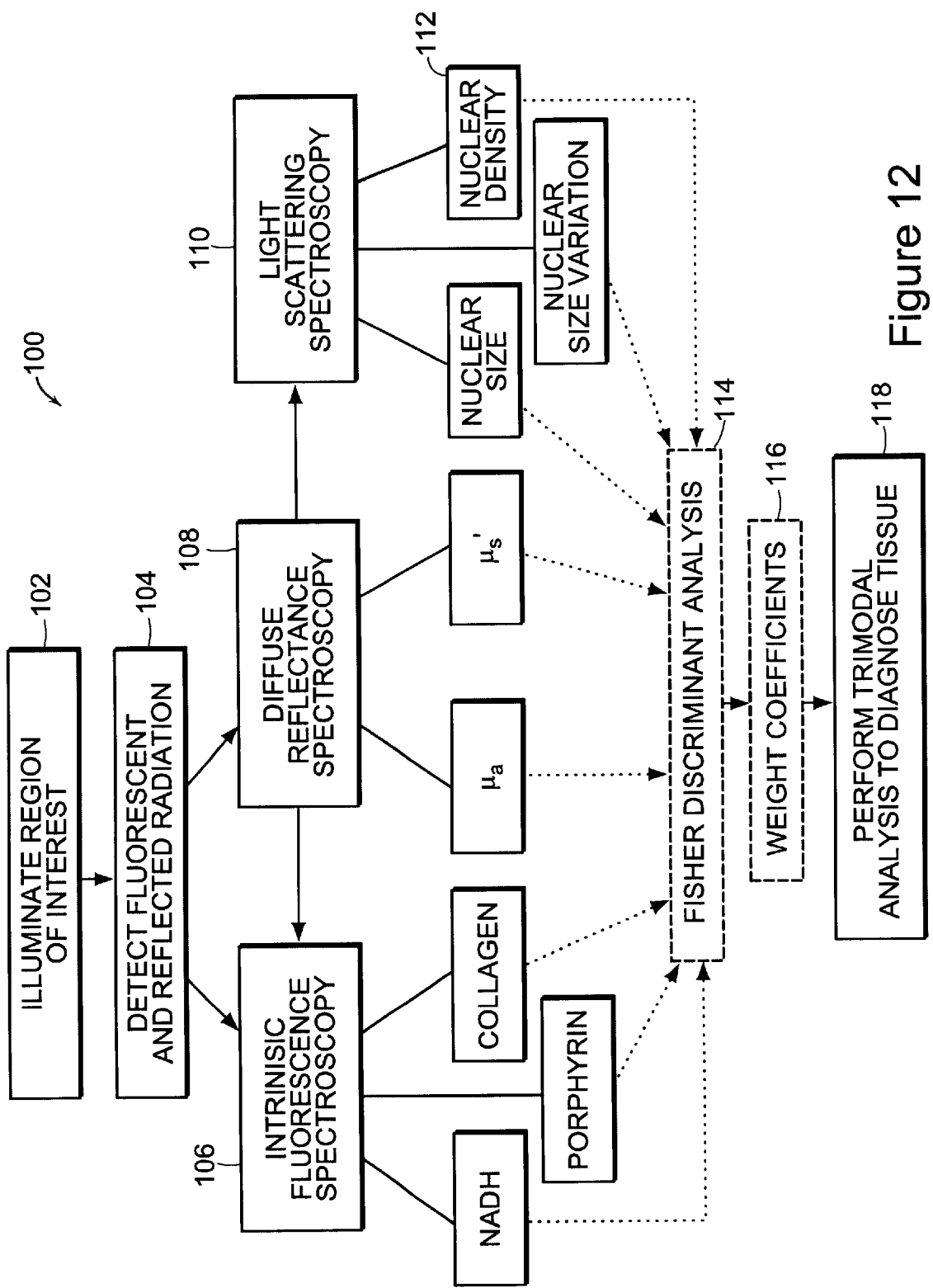
FIG. 12 illustrates a process sequence in accordance with the invention.

FIG. 12 illustrates a process sequence 100 of a preferred embodiment of the invention in which a region of interest within a lumen of a patient is illuminated 102 and the fluorescent and reflected light is detected 104. The three components 106, 108 and 110 are used to generate structural and biochemical information 112. This data can be analyzed using discriminant analysis 114, the components weighted 116, and a diagnosis performed 118 in real-time. These measurements demonstrate the ability of spectroscopic techniques to provide useful information for disease classification in a non-invasive manner. While each of the techniques can be used for detecting dysplasia in Barrett's esophagus, their combination allows the formation of a comprehensive picture of the biochemical and morphological state of tissue. Specifically, decomposition of the intrinsic tissue fluorescence EEMs into EEMs of biochemicals such as NADH and collagen can provide details about tissue biochemistry. Reflectance and light scattering spectroscopy yield morphological information related to the connective tissue and the epithelial cell nuclei. As this information is free from artifacts introduced by tissue excision and processing, it can help advance the understanding of the processes that lead to the progression of dysplasia. Software for performing data analysis in real-time enables the applicability of these techniques as a guide to biopsy. Methods to image regions of interest using this procedure enables large tissue areas to be studied rapidly.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of measuring a structure in a layer of tissue comprising:
    directing incident radiation from a broadband light source onto a region of interest in the layer of tissue;
    collecting fluorescent and reflected radiation from the tissue at a plurality of wavelengths;
    detecting the collected radiation to provide a fluorescence spectrum, a reflectance spectrum and a scattered spectrum as a function of wavelength; and
    determining a plurality of characteristics including a size of a structure within the tissue layer with the measured spectra.

2. The method of claim 1 further comprising determining if the region of interest includes dysplastic tissue.

3. The method of claim 1 further comprising directing radiation onto the tissue using a fiber optic probe.

4. The method of claim 1 further comprising collecting radiation from the tissue using a fiber optic probe.

5. The method of claim 1 further comprising determining an average nuclear size of nuclei within the region of interest.

6. The method of claim 1 further comprising measuring a diameter of a tissue nucleus within the region of interest.

7. The method of claim 1 further comprising measuring a periodic component of an intensity of radiation from the tissue as a function of wavelength.

8. The method of claim 7 further comprising determining the size of a nucleus in the tissue from the periodic component.

9. A method of optically measuring tissue comprising:
   directing incident radiation onto a region of interest in tissue to be measured;
   collecting fluorescent and diffusely reflected radiation from the tissue; and
   measuring a periodic component of collected radiation as a function of wavelength for generating a scattered spectrum to determine a physical characteristic of the tissue.

10. The method of claim 9 further comprising determining if the region of interest includes dysplastic tissue.

11. The method of claim 9 further comprising directing radiation onto the tissue using a fiber optic probe.

12. The method of claim 9 further comprising collecting the radiation from the tissue with a fiber optic probe.

13. The method of claim 9 further comprising determining an average nuclear size of nuclei within the region of interest.

14. The method of claim 9 further comprising measuring a diameter of a tissue nucleus within the region of interest.

15. The method of claim 9 further comprising collecting radiation with an endoscope, the endoscope having an imaging sensor at a distal end of the endoscope.

16. The method of claim 9 further comprising determining a density of nuclei in the tissue from the periodic component.

17. A method of determining a presence of dysplasia in tissue comprising:
   directing incident radiation onto a region of interest in an epithelial layer of tissue;
   collecting fluorescent and backscattered radiation from the tissue;
   detecting the collected fluorescent and backscattered radiation with a detector;
   determining a size of a structure within the epithelial layer of tissue using the detected fluorescent and backscattered radiation; and
   determining the presence of dysplasia in the region of interest of the tissue.

18. The method of claim 17 further comprising determining if the region of interest include dysplastic tissue.

19. The method of claim 17 further comprising collecting radiation in the range of 350 nm to 700 nm.

20. The method of claim 17 further comprising collecting the radiation from the tissue with a fiber optic probe.

21. The method of claim 17 further comprising determining an average nuclear size of nuclei within the region of interest.

22. The method of claim 17 further comprising measuring a diameter of a tissue nucleus within the region of interest.

23. The method of claim 17 further comprising measuring a periodic component of an intensity of scattered radiation from the tissue as a function of wavelength.

24. The method of claim 17 further comprising determining the size of a nucleus in the tissue from the periodic component.

25. A method of optically measuring a material comprising:
   directing incident radiation onto a region of interest in the material to be measured;
   collecting fluorescent and reflected radiation from the material;
   detecting a fluorescence spectrum and a reflectance spectrum from the collected radiation; and
   measuring a periodic component of the detected reflectance spectrum as a function of wavelength to determine a scattered spectrum and to further process and generate a plurality of physical and biochemical characteristics of the material from the fluorescence spectrums and the reflectance spectrum and the scattered spectrum.

26. The method of claim 25 further comprising directing radiation onto the material using a fiber optic probe.

27. The method of claim 25 further comprising collecting the radiation from the material with a fiber optic probe, the probe having an optical fiber with a numerical aperture in a range of 0.05–0.25.

28. The method of claim 25 further comprising determining an average nuclear size of nuclei within the region of interest.

29. The method of claim 25 further comprising measuring a number of particles per unit area within the region of interest.

30. An apparatus for optically measuring tissue comprising:
   a first radiation source and a second radiation source that illuminate a region of interest in tissue to be measured with incident radiation;
   an optical system that collects fluorescence and reflected radiation from the tissue;
   a detector system that senses the collected fluorescence and reflected radiation; and
   a data processor that determines a periodic component of detected radiation as a function of wavelength to generate a scattering spectrum to determine a physical characteristic of the tissue.

31. The apparatus of claim 30 further comprising a filter wheel and a broadband light source that generates light in a range of 350–700 nm.

32. The apparatus of claim 30 further comprising a fiber optic probe that couples the first radiation source and the second radiation source to a single region of interest on the tissue.

33. The apparatus of claim 30 wherein the data processor generates a modulated fluorescence spectrum with collected fluorescence and reflected radiation.

34. The apparatus of claim 33 wherein the probe is insertable in an endoscope.

35. The method of measuring a size and composition of a structure in a layer of tissue comprising:
   directing incident radiation onto a region of interest in the layer of tissue;
   collecting fluorescence and reflected radiation from the tissue;
   detecting the collected fluorescence and reflected radiation; and
   identifying and determining an average nuclear size of nuclei within the region of interest using the detected radiation.

36. The method of claim 35 further comprising determining if the region of interest includes dysplastic tissue.

37. The method of claim 35 further comprising directing radiation onto the tissue using a fiber optic probe.

38. The method of claim 35 further comprising collecting the radiation from the tissue with a fiber optic probe.

39. The method of claim 35 further comprising measuring a diameter of a tissue nucleus within the region of interest.

40. The method of claim 35 further comprising measuring a periodic component of an intensity of radiation from the tissue as a function of wavelength.

41. The method of claim 40 further comprising determining the size of a nucleus in the tissue from the periodic component.

42. A method of measuring a structure in a layer of tissue comprising:

directing incident radiation onto a region of interest in the layer of tissue;

collecting fluorescent and reflected radiation from the tissue;

detecting the collected radiation;

generating a scattered spectrum from the reflected radiation;

measuring a size of a tissue component in the region of interest with the scattered spectrum; and processing a fluorescence spectrum with a reflectance spectrum to provide a modified fluorescence spectrum.

43. The method of claim 42 further comprising determining if the region of interest includes dysplastic tissue.

44. The method of claim 42 further comprising directing radiation onto the tissue using a fiber optic probe.

45. The method of claim 42 further comprising collecting the radiation from the tissue with a fiber optic probe.

46. The method of claim 42 further comprising determining an average nuclear size of nuclei within the region of interest.

47. The method of claim 42 further comprising measuring a periodic component of an intensity of radiation from the tissue as a function of wavelength.

48. The method of claim 47 further comprising determining the size of a nucleus in the tissue from the periodic component.

* * * * *

UNITED STATES PATENT AND TRADEMARK OFFICE
CERTIFICATE OF CORRECTION

PATENT NO.         : 6,697,652 B2
APPLICATION NO.    : 09/766879
DATED              : February 24, 2004
INVENTOR(S)        : Irene Georgakoudi et al.

It is certified that error appears in the above-identified patent and that said Letters Patent is hereby corrected as shown below:

Column 1, following "GOVERNMENT SUPPORT" please delete lines 7-10 and insert the new paragraph as follows:

--This invention was made with government support under Grant Nos. P41 RR002594 and R01 CA053717, awarded by the National Institutes of Health. The government has certain rights in this invention.--

Signed and Sealed this
Tenth Day of May, 2011

David J. Kappos
*Director of the United States Patent and Trademark Office*